(12) United States Patent
Lu et al.

(10) Patent No.: US 9,193,718 B2
(45) Date of Patent: Nov. 24, 2015

(54) QUINAZOLINE DERIVATIVE AND APPLICATION THEREOF

(75) Inventors: Canzhong Lu, Fujian (CN); Jianping Yong, Fujian (CN)

(73) Assignee: FUJIAN INSTITUTE OF RESEARCH ON THE STRUCTURE OF MATTER, CHINESE ACADEMY OF SCIENCES, Fuzhou, Fujian (CN)

( * ) Notice: Subject to any disclaimer, the term of this patent is extended or adjusted under 35 U.S.C. 154(b) by 0 days.

(21) Appl. No.: 14/241,067

(22) PCT Filed: Mar. 26, 2012

(86) PCT No.: PCT/CN2012/073051
§ 371 (c)(1),
(2), (4) Date: Feb. 25, 2014

(87) PCT Pub. No.: WO2013/143057
PCT Pub. Date: Oct. 3, 2013

(65) Prior Publication Data
US 2014/0221402 A1    Aug. 7, 2014

(51) Int. Cl.
*A61K 31/517* (2006.01)
*C07D 413/12* (2006.01)
*C07D 413/06* (2006.01)

(52) U.S. Cl.
CPC ............ *C07D 413/12* (2013.01); *C07D 413/06* (2013.01)

(58) Field of Classification Search
None
See application file for complete search history.

(56) References Cited

PUBLICATIONS

CA Registry No. 930023-01-1, entered into the Registry File on Apr. 13, 2007, supplied by Enamine Chemical Library.*

EnamineStore, 1 page retrieved from the Internet at http://www.enamine.net/index.php?option=com_content&task=view&id=22 on Jan. 9, 2015.*

* cited by examiner

*Primary Examiner* — Emily Bernhardt
(74) *Attorney, Agent, or Firm* — Novick, Kim & Lee, PLLC; Allen Xue

(57) ABSTRACT

This invention provides a class of quinazoline compounds, as represented by formula (I), and their pharmaceutically acceptable salts,

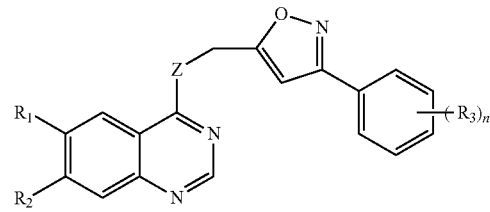

(I)

wherein: each of $R_1$ and $R_2$ independently, is selected from H, $C_1$-$C_6$ alkoxy, halo-$C_1$-$C_6$ alkoxy, $C_1$-$C_6$-alkoxy-$C_1$-$C_6$ alkoxy, $C_3$-$C_8$ cycloalkoxy, $C_3$-$C_8$ heterocycloalkoxy containing at least one of heteroatoms selected from N, O, S; Z is —$NR_4$—, $C(R_5)_2$, S or —O—, wherein $R_4$ is H or $C_1$-$C_3$ alkyl, $R_5$ is the same or different, selected from H or $C_1$-$C_3$ alkyl; $R_3$ is selected from H, halogen, $C_1$-$C_6$ alkyl, $C_1$-$C_6$ alkoxy or halo-$C_1$-$C_6$ alkyl; n is an integer from 0 to 5. This invention also provides methods of preparation and medical uses of the compounds of formula (I) and their pharmaceutically acceptable salts. These compounds have the activity of inhibiting EGFR-TK, and can be used as drugs for the treatment of protein tyrosine kinase related diseases such as tumors, cancers, etc.

10 Claims, No Drawings

QUINAZOLINE DERIVATIVE AND APPLICATION THEREOF

TECHNICAL FIELD

The present invention relates to a class of quinazoline derivatives with a novel structure comprising isoxazole heterocycle, pharmaceutical compositions comprising these quinazoline derivatives and use thereof, and in particular relates to quinazoline derivatives or their pharmaceutical compositions having the activity of inhibiting epidermal growth factor receptor protein tyrosine kinase (EGFR-TK). Such substances can be used as drugs for treating protein tyrosine kinase related diseases such as tumours, cancers.

BACKGROUND ART

Binding of epidermal growth factor to epidermal growth factor receptor can activate the activity of tyrosine kinase, and in consequence may activate reactions that lead to cellular proliferation. Overexpression and overactivity of EGFR may cause uncontrollable cell division.

The epidermal growth factor receptor tyrosine kinase (EGFR-TK), the first discovered protein tyrosine kinase, is widely distributed in human tissue cell membranes and overexpresses in most of tumours (e.g. bladder cancer, non-small cell lung cancer, ovarian cancer, breast cancer, stomach cancer, esophageal cancer and so on). There is an adenosine triphosphate (ATP) binding site in EGFR intracellular region. Therefore, EGFR inhibitors may competitively bind to the ATP binding site, and thereby inhibit EGFR phosphorylation, block the downstream signal transduction and in turn inhibits the growth, differentiation and metastasis of tumour cells. Nowadays the targeted tumour therapy based on EGFR receptor as a target is one of active research areas in cancer treatment. In clinical studies it has also achieved remarkable results, in which the research of small molecular compounds based on quinazoline as a nucleus is most prominent.

Some quinazoline compounds, which bear a phenylamino substituent at the 4-position and substituents at the 6- and/or 7-position, are disclosed to have activity to inhibit receptor tyrosine kinase in Patent Application Publication Nos. WO96/33977, WO96/33978, WO96/33979, WO96/33980, WO96/33981, WO97/30034, WO97/30035, WO97/38994, WO98/13354, WO00/55141, WO00/56720, WO02/41882, WO03/82290, EP566226 and EP837063. All the above-mentioned documents are hereby incorporated herein by reference.

4-(2,3-dihalophenylamino)quinazoline compounds substituted by heterocyclyloxy group or heterocycloalkoxy groups at 6-position are disclosed in Patent Application Publication No. WO03/082831. Said compounds are inhibitors of erbB, particularly EGFR tyrosine kinase. The above-mentioned document is hereby incorporated herein by reference.

Small molecular drugs for anti-tumour based on EGFR acceptors and comprising quinazoline as a nucleus, for example, gefitinib (Iressa), erlotinib and lapatinib have been successively approved by FDA for clinical uses. In China Dr. Yinxiang Wang and Dr. Lieming Ding developed an EGFR acceptor inhibitor, icotinib (Conmana), based on erlotinib (Tarceva). The third-period clinical trial showed that icotinib (Conmana) has an efficacy equal to erlotinib and better safety, and its dosage and regimen of administration are more suitable for Chinese. Icotinib was approved to be used for treating advanced non-small cell lung cancer by the Chinese food and Drug Administration in June 2011.

The present invention is based on erlotinib and icotinib. A class of quinazoline compounds containing isoxazole heterocycles has been synthesized, wherein isoxazole heterocycle is introduced into the nucleus of quinazoline. The in vitro activity of inhibiting epidermal growth factor receptor tyrosine kinase (EGFR-TK) of this class of compounds has shown that said compounds have more strong activity of inhibiting EGFR-TK, and can be used as anti-tumour drugs or lead compounds.

DETAILED DESCRIPTION OF THE INVENTION

The present invention aims to provide quinazoline compounds containing isoxazole heterocycle, as represented by formula (I). The activity study shows that these compounds, which can be used as active ingredient, have the activity of inhibiting EGFR-TK.

This invention is realized by the following technical solutions:

A quinazoline compound as represented by formula (I) or their pharmaceutically acceptable salts,

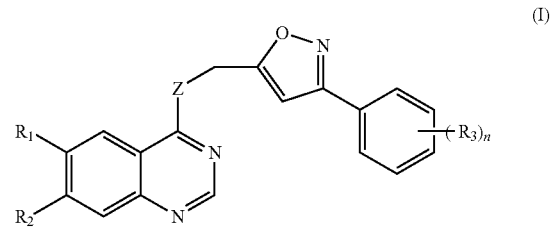

wherein: each of $R_1$ and $R_2$ independently, is selected from H, $C_1$-$C_6$ alkoxy, halo-$C_1$-$C_6$ alkoxy, $C_1$-$C_6$-alkoxy-$C_1$-$C_6$ alkoxy, $C_3$-$C_8$ cycloalkoxy, $C_3$-$C_8$ heterocycloalkoxy containing at least one of heteroatoms selected from N, O, S;

Z is —$NR_4$—, $C(R_5)_2$, S or —O—, wherein $R_4$ is H or $C_1$-$C_3$ alkyl, $R_5$ is the same or different, selected from H or $C_1$-$C_3$ alkyl;

$R_3$ is selected from H, halo, $C_1$-$C_6$ alkyl, $C_1$-$C_6$ alkoxy or halo-$C_1$-$C_6$ alkyl; n is an integer from 0 to 5.

According to a preferred technical solution of the present invention, wherein in formula (I):

$R_1$ and $R_2$ are selected from H, $C_1$-$C_3$ alkoxy, $C_1$-$C_6$ alkoxy-$C_1$-$C_6$ alkoxy, $C_3$-$C_8$ heterocycloalkoxy containing at least one of heteroatoms selected from N, O, S;

Z is —NH—, $CH_2$, or —O—;

$R_3$ is selected from H, fluoro, chloro, bromo, methyl, methoxy or trifluoromethyl; n is preferably selected from 1 to 4, and more preferably from 2 to 3.

According to a more preferred technical solution of the present invention, wherein in formula (I):

Z is —NH— or —O—;

$R_1$ and $R_2$ are selected from H, $C_1$-$C_3$ alkoxy, $C_1$-$C_3$ alkoxy-$C_1$-$C_3$ alkoxy;

$R_3$ is preferably at the ortho- or para-position in the isoxazole ring, and more preferably 4-fluoro, 4-chloro, 2-chloro, 4-bromo, 2,4-dichloro, 4-methyl, 4-methoxy, H, 4-trifluoromethyl or 2,4-dimethoxy.

According to the present invention, said quinazoline compounds of formula (I) are more preferably selected from any of the following compounds:
4-((3-phenyl-isoxazol-5-yl)-methoxy-)-quinazoline;
4-((3-(4-fluorophenyl)-isoxazol-5-yl))-methoxy-)-quinazoline;

4-((3-(4-chlorophenyl)-isoxazol-5-yl))-methoxy-)-quinazoline;
4-((3-(2-chlorophenyl)-isoxazol-5-yl))-methoxy-)-quinazoline;
4-((3-(4-bromophenyl)-isoxazol-5-yl))-methoxy-)-quinazoline;
4-((3-(2,4-dichlorophenyl)-isoxazol-5-yl))-methoxy-)-quinazoline;
4-((3-(4-methylphenyl)-isoxazol-5-yl))-methoxy-)-quinazoline;
4-((3-(4-methoxyphenyl)-isoxazol-5-yl))-methoxy-)-quinazoline;
4-((3-(4-trifluoromethylphenyl)-isoxazol-5-yl))-methoxy-)-quinazoline;
4-((3-(2,4-dimethoxyphenyl)-isoxazol-5-yl))-methoxy-)-quinazoline;
6,7-dimethoxy-4-((3-phenyl-isoxazol-5-yl)-methoxy-)-quinazoline;
6,7-dimethoxy-4-((3-(4-fluorophenyl)-isoxazol-5-yl))-methoxy-)-quinazoline;
6,7-dimethoxy-4-((3-(4-chlorophenyl)-isoxazol-5-yl))-methoxy-)-quinazoline;
6,7-dimethoxy-4-((3-(2-chlorophenyl)-isoxazol-5-yl))-methoxy-)-quinazoline;
6,7-dimethoxy-4-((3-(4-bromophenyl)-isoxazol-5-yl))-methoxy-)-quinazoline;
6,7-dimethoxy-4-((3-(2,4-dichlorophenyl)-isoxazol-5-yl))-methoxy-)-quinazoline;
6,7-dimethoxy-4-((3-(4-methylphenyl)-isoxazol-5-yl))-methoxy-)-quinazoline;
6,7-dimethoxy-4-((3-(4-methoxyphenyl)-isoxazol-5-yl))-methoxy-)-quinazoline;
6,7-dimethoxy-4-((3-(4-trifluoromethylphenyl)-isoxazol-5-yl))-methoxy-)-quinazoline;
6,7-dimethoxy-4-((3-(2,4-dimethoxyphenyl)-isoxazol-5-yl))-methoxy-)-quinazoline;
(6,7-bis(2-methoxyethoxy))-4-((3-phenyl-isoxazol-5-yl)-methoxy-)-quinazoline;
(6,7-bis(2-methoxyethoxy))-4-((3-(4-fluorophenyl)-isoxazol-5-yl))-methoxy-)-quinazoline;
(6,7-bis(2-methoxyethoxy))-4-((3-(4-chlorophenyl)-isoxazol-5-yl))-methoxy-)-quinazoline;
(6,7-bis(2-methoxyethoxy))-4-((3-(2-chlorophenyl)-isoxazol-5-yl))-methoxy-)-quinazoline;
(6,7-bis(2-methoxyethoxy))-4-((3-(4-bromophenyl)-isoxazol-5-yl))-methoxy-)-quinazoline;
(6,7-bis(2-methoxyethoxy))-4-((3-(2,4-dichlorophenyl)-isoxazol-5-yl))-methoxy-)-quinazolin;
(6,7-bis(2-methoxyethoxy))-4-((3-(4-methylphenyl)-isoxazol-5-yl))-methoxy-)-quinazoline;
(6,7-bis(2-methoxyethoxy))-4-((3-(4-methoxyphenyl)-isoxazol-5-yl))-methoxy-)-quinazoline;
(6,7-bis(2-methoxyethoxy))-4-((3-(4-trifluoromethylphenyl)-isoxazol-5-yl))-methoxy-)-quinazoline;
(6,7-bis(2-methoxyethoxy))-4-((3-(2,4-dimethoxyphenyl)-isoxazol-5-yl))-methoxy-)-quinazoline;
4-((3-phenyl-isoxazol-5-yl)-methylamino-)-quinazoline;
4-((3-(4-fluorophenyl)-isoxazol-5-yl))-methylamino-)-quinazoline;
4-((3-(4-chlorophenyl)-isoxazol-5-yl))-methylamino-)-quinazoline;
4-((3-(2-chlorophenyl)-isoxazol-5-yl))-methylamino-)-quinazoline;
4-((3-(4-bromophenyl)-isoxazol-5-yl))-methylamino-)-quinazoline;
4-((3-(2,4-dichlorophenyl)-isoxazol-5-yl))-methylamino-)-quinazoline;
4-((3-(4-methylphenyl)-isoxazol-5-yl))-methylamino-)-quinazoline;
4-((3-(4-methoxyphenyl)-isoxazol-5-yl))-methylamino-)-quinazoline;
4-((3-(4-trifluoromethylphenyl)-isoxazol-5-yl))-methylamino-)-quinazoline;
4-((3-(2,4-dimethoxyphenyl)-isoxazol-5-yl))-methylamino-)-quinazoline;
6,7-dimethoxy-4-((3-phenyl-isoxazol-5-yl)-methylamino-)-quinazoline;
6,7-dimethoxy-4-((3-(4-fluorophenyl)-isoxazol-5-yl))-methylamino-)-quinazoline;
6,7-dimethoxy-4-((3-(4-chlorophenyl)-isoxazol-5-yl))-methylamino-)-quinazoline;
6,7-dimethoxy-4-((3-(2-chlorophenyl)-isoxazol-5-yl))-methylamino-)-quinazoline;
6,7-dimethoxy-4-((3-(4-bromophenyl)-isoxazol-5-yl))-methylamino-)-quinazoline;
6,7-dimethoxy-4-((3-(2,4-dichlorophenyl)-isoxazol-5-yl))-methylamino-)-quinazoline;
6,7-dimethoxy-4-((3-(4-methylphenyl)-isoxazol-5-yl))-methylamino-)-quinazoline;
6,7-dimethoxy-4-((3-(4-methoxyphenyl)-isoxazol-5-yl))-methylamino-)-quinazoline;
6,7-dimethoxy-4-((3-(4-trifluoromethylphenyl)-isoxazol-5-yl))-methylamino-)-quinazoline;
6,7-dimethoxy-4-((3-(2,4-dimethoxyphenyl)-isoxazol-5-yl))-methylamino-)-quinazoline;
(6,7-bis(2-methoxyethoxy))-4-((3-phenyl-isoxazol-5-yl)-methylamino-)-quinazoline;
(6,7-bis(2-methoxyethoxy))-4-((3-(4-fluorophenyl)-isoxazol-5-yl))-methylamino-)-quinazoline;
(6,7-bis(2-methoxyethoxy))-4-((3-(4-chlorophenyl)-isoxazol-5-yl))-methylamino-)-quinazoline;
(6,7-bis(2-methoxyethoxy))-4-((3-(2-chlorophenyl)-isoxazol-5-yl))-methylamino-)-quinazoline;
(6,7-bis(2-methoxyethoxy))-4-((3-(4-bromophenyl)-isoxazol-5-yl))-methylamino-)-quinazoline;
(6,7-bis(2-methoxyethoxy))-4-((3-(2,4-dichlorophenyl)-isoxazol-5-yl))-methylamino-)-quinazolin;
(6,7-bis(2-methoxyethoxy))-4-((3-(4-methylphenyl)-isoxazol-5-yl))-methylamino-)-quinazoline;
(6,7-bis(2-methoxyethoxy))-4-((3-(4-methoxyphenyl)-isoxazol-5-yl))-methylamino-)-quinazoline;
(6,7-bis(2-methoxyethoxy))-4-((3-(4-trifluoromethylphenyl)-isoxazol-5-yl))-methylamino-)-quinazoline;
(6,7-bis(2-methoxyethoxy))-4-((3-(2,4-dimethoxyphenyl)-isoxazol-5-yl))-methylamino-)-quinazoline.

The quinazoline compounds represented by formula (I) can be selected respectively to form pharmaceutically acceptable salts with pharmaceutically acceptable acids. Here the term "pharmaceutically acceptable salts" not only includes salts formed with inorganic acids, such as hydrochloride, phosphate, diphosphate, hydrobromide, sulfate, sulfinate, nitrate, and similar salts; but also includes salts formed with organic acids, such as lactate, oxalate, malate, maleate, fumarate, tartrate, succinate, citrate, lactate, sulfonate, p-toluenesulfonate, 2-hydroxyethyl sulfonate, benzoate, salicylate, stearate, trifluoroacetate or amino acid salt and alkanoate such as acetate, $HOOC-(CH_2)_n-COOH$ salt where n is 0-4, and similar salts. Similarly, pharmaceutically acceptable cations include, but are not limited to, sodium, potassium, calcium, aluminum, lithium and ammonium.

The present invention also provides a kind of pharmaceutical composition, comprising a quinazoline compound represented by any of the above formula (I) or its pharmaceutically acceptable salt, and at least one pharmaceutically acceptable, inert, non-toxic excipient or carrier.

The present invention also provides quinazoline compounds represented by any of the above formula (I) or their pharmaceutically acceptable salt which are used as drug, particularly an anti-tumour drug used for effectively inhibiting the overexpression and/or overactivity of EGFR.

The present invention also provides the use of the quinazoline compounds represented by any of the above formula (I) or their pharmaceutically acceptable salt in the preparation of the drugs for anti-tumour or anti-cancer.

According to the present invention, said tumours or cancers are the cancers related to overexpression and/or overactivity of EGFR. The tumours or cancers are more preferably selected from bladder cancer, non-small cell lung cancer, ovarian cancer, breast cancer, stomach cancer, esophageal cancer, lung cancer, head and neck cancer, colon cancer, pharyngeal cancer and pancreatic cancer, and so on, more preferably the use in non-small cell lung cancer.

The present invention also provides the use of the quinazoline compounds represented by any of the above formula (I) or their pharmaceutically acceptable salt in the preparation of the inhibitors for inhibiting the overexpression and/or overactivity of EGFR.

The present invention also provides a method of preparation of the quinazoline compounds containing isoxazole heterocycle represented by formula (I), characterized in that said method comprises the following steps:

6,7-Disubstituted-4-chloro-quinazoline (formula II) and 3-substituted phenyl-5-hydroxymethyl-isoxazole (formula III) or 3-substituted phenyl-5-aminomethyl-isoxazole (formula IV) used as starting materials are reacted in a system of a dry organic solvent and an alkaline deacid reagent to prepare said compounds.

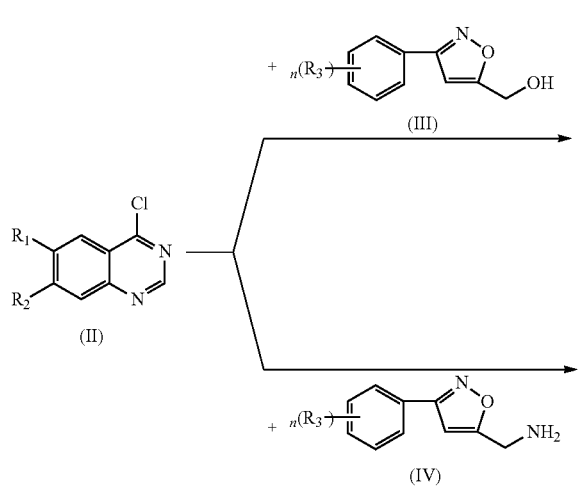

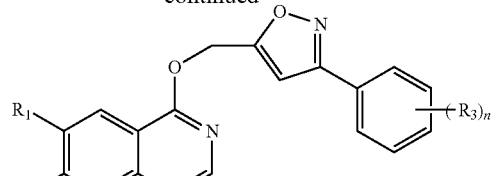

(I-1)

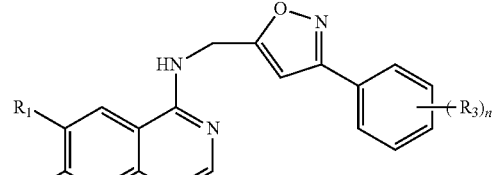

(I-2)

If needed, any functional group in formula (II) can be protected;
and afterward, if needed (in any order):
(1) removing any protecting group, and
(2) forming the pharmaceutically acceptable salt of the compounds of formula I.

According to the present invention, the reaction temperature is from −20° C. to reflux condition, preferably from room temperature to reflux condition.

According to the present invention, the organic solvent is benzene, toluene, xylene, dichloromethane, chloroform, isopropanol, tetrahydrofuran or DMF, more preferably, isopropanol.

According to the present invention, the alkaline deacid reagent is an organic base or an inorganic base. The organic base is preferably triethylamine, tripropylamine, DMAP, potassium tert-butoxide, etc; and the inorganic base is preferably potassium carbonate, sodium hydride, sodium carbonate, etc. The deacid reagent is preferably triethylamine.

According to the present invention, the intermediate 6,7-disubstituted-4-chloro-quinazoline of the above-described formula (II) can be prepared by the following method:

starting material 6,7-disubstituted-quinazolinone is refluxed in a system of thionyl chloride or phosphorus oxychloride ($R_1$, $R_2$ are defined as above):

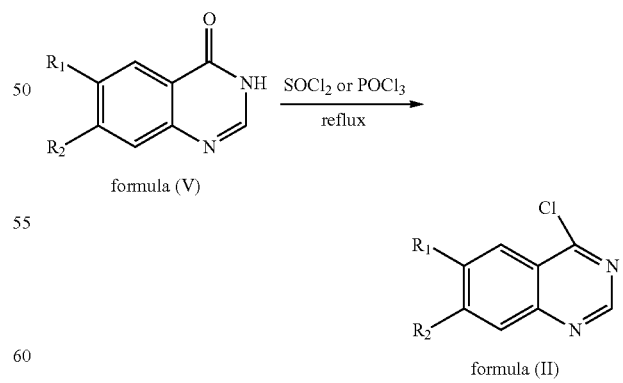

According to the present invention, the intermediate 3-substituted phenyl-5-hydroxymethyl-isoxazole of formula (III) or the intermediate 3-substituted phenyl-5-aminomethyl-isoxazole of formula (IV) can be prepared by the following method:

the target compound can be prepared via the synthesis of oxime, 1,3-dipolar cycloaddition reaction, methanesulfonyl esterification, azidation and reduction from substituted benzaldehyde as a start material ($R_3$ is defined as above). The detailed process can be found in the following procedure:

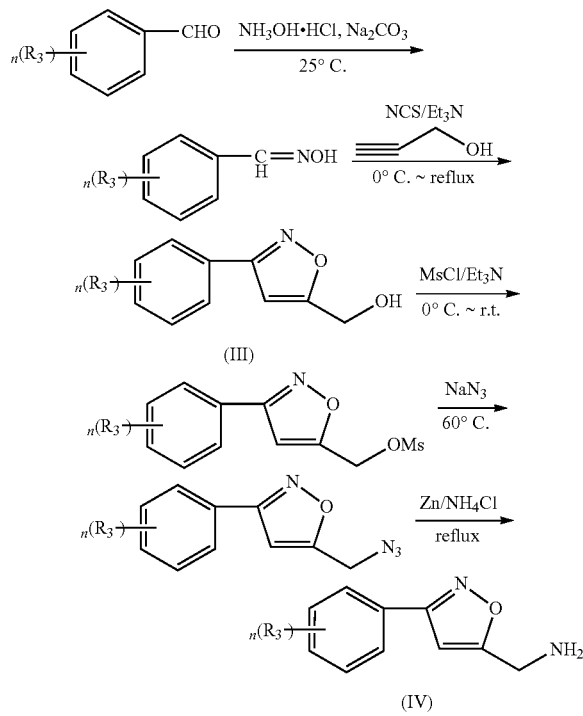

Meanwhile, as to the compounds where Z is another substituent, for instance $CH_2$, S, said compounds can be prepared using the corresponding propargylchloride, propargyl mercaptan.

The compounds of formula (I) according to the invention include, but not limited to, their optical isomers, racemates, and mixtures thereof.

The $C_3$-$C_8$ cycloalkyl group of the $C_3$-$C_8$ cycloalkoxy according to the invention can be cyclopropyl, cyclobutyl, cyclopentyl, cyclohexyl, cycloheptyl, cyclooctyl, preferably cyclopropyl, cyclopentyl or cyclohexyl.

The $C_3$-$C_8$ heterocycloalkyl of the $C_3$-$C_8$ heterocycloalkoxy containing at least one of heteroatoms selected from N, O, S according to the invention can be piperazinyl, piperidinyl, morpholinyl, pyrrolidinyl, homopiperazinyl, preferably piperazinyl, morpholinyl or piperidinyl.

The term "an effective amount" refers to the amount of said at least one compound and/or at least one pharmaceutically acceptable salt that is effective for the "treatment" of an individual disease or discomfort. If it is a cancer, the effective amount may reduce the number of cancer or tumour cells; reduce the size of the tumour; inhibit or stop the tumour cell infiltration into peripheral organs, for example, the spread of tumours into soft tissue or bone; inhibit or stop tumour metastasis; inhibit or stop tumour growth; relieve to a certain extent one or more symptoms associated with cancer; reduce morbidity and mortality; improve quality of life; or a combination of such effects. The effective amount may be an amount sufficient to decrease the symptoms of a disease by inhibiting EGFR activity. For cancer therapy, the effect of in vivo experiments can be determined by assessing, such as survival period, time to disease progression (TTP), response rates (RR), the duration of sustained response and/or quality of life. The effective amount may vary, as recognized by those professionals, depending on route of administration, excipient dosage, and the combination with other drugs.

The term "an effective amount" may also refer to an amount of at least one described compound and/or at least one pharmaceutically acceptable salt that is effective to inhibit over-expression and/or overactivity of EGFR.

EXAMPLES

Hereinafter, the present invention will be further illustrated with reference to the examples. It should be noted that the following examples cannot constitute a limitation to the scope of the present invention. Any modification based on the present invention would not depart from the spirits of the present invention.

Among them, the synthetic processes of intermediates and target compounds are illustrated by those in the examples, and the synthetic processes of other intermediates and target compounds are the same as those of the representative compounds.

Instruments and Reagents:

AVANCE III NMR spectrometer (400 MHz, DMSO-d6, TMS internal standard), ion trap liquid chromatography mass spectrometer (DECAX-30000 LCQ Deca XP), Shimadzu FTIR-8400S spectrometer (producted by Shimadzu Corporation, Japan), XT5 micro melting point detector with digital display (manufactured by Beijing Keyi electro-optical Instrument Plant, temperature uncorrected), wavelength-tunable microplate reader (Molecular Devies SPECTRAMAX190).

Tyrosine kinase (EGFR) was expressed using a baculovirus expression system, and purified by using a Ni-NTA affinity chromatography. After tested, it was consistent with experimental standard. Poly(Glu,Tyr)$_{4:1}$ (Sigma), Monoclonal Anti-Phosphotyrosine antibody PY99 (Santa Cruz), horseradish peroxidase-labeled goat anti-mouse IgG (Calbiochem), ATP, DTT, OPD (Amresco), microplates (Corning). Other reagents were all commercially available with analytical grade purity, which were not treated before use if no special instructions present. Isopropanol was dried with molecular sieves before use.

Example 1

Synthesis of 6,7-dimethoxy-4-chloro-quinazoline 4.12 g (20 mmol) of 6,7-dimethoxy-4-chloro-quinazolinone was placed in a 500 mL single-necked round-bottom flask, and then 120 mL of distilled thionyl chloride containing a drop of DMF was slowly added. The mixture was refluxed. After the completion of the reaction monitored by TLC, the excess amount of thionyl chloride was evaporated under reduced pressure. The residue was dissolved in 300 mL of ethyl acetate, and then washed to neutrality with saturated sodium bicarbonate solution. The organic layer was dried over anhydrous sodium sulfate, concentrated, and then purified by column chromatography (Vpetroleum ether:Vethyl acetate=4:1-2:1) to give 6,7-dimethoxy-4-chloro-quinazoline in 85% yield. $^1$H NMR (DMSO-$d_6$, 400 MHz): 4.01 (s, 6H, 2CH$_3$), 7.38 (s, 1H), 7.45 (s, 1H), 8.88 (s, 1H); ESI-MS (100%): 224 ((M)$^+$, 100).

Example 2

Synthesis of the intermediate 3-substituted phenyl-5-hydroxymethyl-isoxazole and 3-substituted phenyl-5-aminomethyl-isoxazole wherein taking R$_3$ is H as an example:

(1) Synthesis of Benzaldehyde Oxime

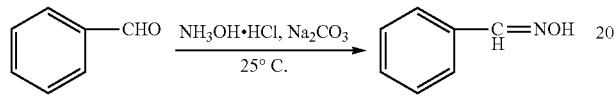

10.0 mmol of benzaldehyde was dissolved in 30 mL of 30% CH$_3$OH solution in H$_2$O and then added into a conical flask equipped with magnetic stirrer. 10.0 mmol of hydroxylamine hydrochloride was added under stirring. After hydroxylamine hydrochloride was dissolved, 5.0 mmol of dry and porphyrized sodium carbonate was slowly added. The reaction was carried out at room temperature. After the completion of the reaction monitored by TLC, the system was evaporated to remove methanol under reduced pressure. The mixture was extracted by the addition of 30 mL H$_2$O, and then dichloromethane (3×30 mL). The organic layers were combined, and then dried over anhydrous sodium sulfate. The solvent was removed to afford a crude product of benzaldehyde oxime in 86.2% yield. The crude material was directly used in the next reaction without separation and purification.

(2) 3-phenyl-5-hydroxymethyl-isoxazole

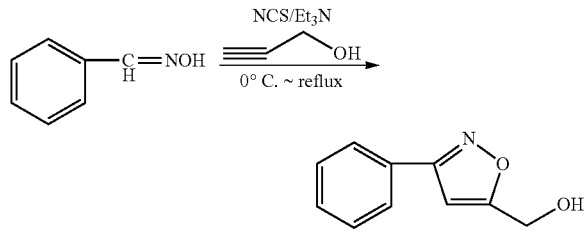

10.0 mmol of benzaldehyde oxime and 30 mL of dry dichloromethane were placed in a 250 mL single-necked round-bottom flask. 1.60 g (12.0 mmol) of N-chlorosuccinimide (NCS) was added under stirring. After NCS was completely dissolved by slightly heating, 0.56 g (10.0 mmol) of 2-propyn-1-ol was added dropwise, and then 20 mL solution of 10.1 g (10.0 mmol) of triethylamine in dichloromethane. After the addition was complete, the system was refluxed. After the completion of the reaction monitored by TLC, the mother liquor was washed with water, dried over anhydrous sodium sulfate, and separated by column chromatography (Vpetroleum ether:Vethyl acetate=5:1-2:1) to give 3-phenyl-5-hydroxymethyl-isoxazole in 76.8% yield.

(3) 3-phenyl-5-aminomethyl-isoxazole

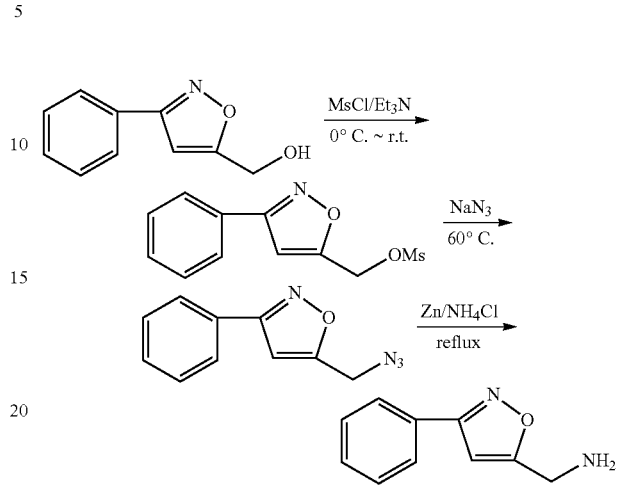

10.0 mmol of 3-Phenyl-5-hydroxymethyl-isoxazole and 30 mL of dry dichloromethane were added in a 250 mL single-necked round-bottom flask. A solution of 1.01 g (10.0 mmol) triethylamine in 20 mL dichloromethane was added into the system under stirring in an ice bath. A solution of 1.37 g (12.0 mmol) of methanesulfonyl chloride (MsCl) in 5 mL of dichloromethane was slowly added dropwise to the system. The reaction was carried out in an ice bath for 2 h, was and then carried out at room temperature. After the completion of the reaction monitored by TLC, the mother liquor was washed with water, 5% sodium bicarbonate solution, and then water again, and dried over anhydrous sodium sulfate. The solvent was removed under reduced pressure to give a crude product of 3-phenyl-isoxazol-5-methyl methanesulfonate in 68.0% yield. The crude material was directly used in the next reaction without purification.

5.0 mmol of 3-phenyl-isoxazol-5-methyl methanesulfonate was dissolved in 20 mL of dry DMF. 0.34 g of (5.20 mmol) sodium azide was added and dissolved in the solution by stirring under room temperature. The mixture was placed in an oil bath of 45-50 to react. After the completion of the reaction monitored by TLC, the mixture was filtered and the filter cake was washed with diethyl ether (2×30 mL). The organic layers were combined and 100 mL of H$_2$O was added into the organic layers which was then extracted with diethyl ether (5×30 mL). The organic layers was combined, washed twice with water, and dried over anhydrous sodium sulfate. The solvent was removed to afford a crude product of 3-phenyl-5-azidemethyl-isoxazole in 90% yield. The crude product was directly carried out in the following reduction reaction.

5.0 mmol of 3-phenyl-5-azidemethyl-isoxazole was dissolved in a mixing solution of 80 mL of ethanol and 20 mL of water. 0.17 g (2.6 mmol) of zinc powder and 0.28 g (5.2 mmol) of NH$_4$Cl were added into the system. After the reaction was refluxed for 1 h, ethanol was removed under vacuum, and then 20 mL of water was added into the system. The mixture was adjusted to pH 12 with 20% sodium hydroxide solution, and 50 mL DCM was added into the system. The reaction mixture was stirred homogeneous and then filtered. The filter residue was dissolved with a small amount of water and then filtered. Two filtrates were combined. The organic layer was separated, washed with water, and dried over anhydrous sodium sulfate. The solvent was removed under vacuum, and the residue was separated by column chromatography (Vdichloromethane:Vmethanol=10:1) to afford 3-phenyl-5-aminomethyl-isoxazole as a pale yellow solid in 75% yield, m.p. 39-40, $^1$H-NMR (400 MHz, CDCl$_3$, TMS), δppm: 1.60 (s, 2H, NH$_2$), 3.91 (s, 2H, CH$_2$), 6.40 (s, 1H), 7.39 (m, 2H, Ar—H), 7.76 (m, 2H, Ar—H).

Example 3

(6,7-bis(2-methoxyethoxy))-4-((3-phenyl-isoxazol-5-yl)-methoxy-)-quinazoline

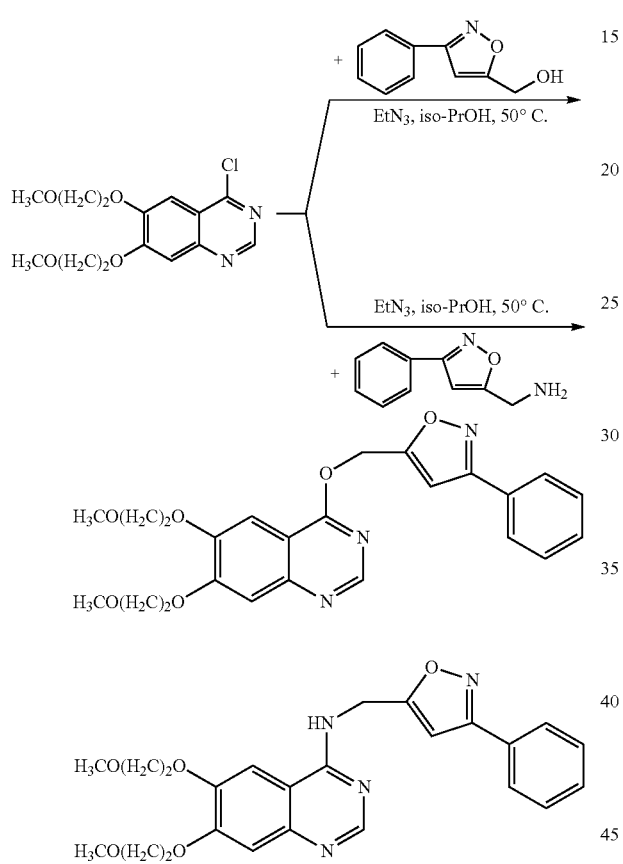

0.3 g (1 mmol) of (6,7-bis(2-methoxyethoxy))-4-chloroquinazoline was dissolved in 5 mL dry isopropanol. Under stirring, a solution of 0.175 g (1 mmol) of 5-hydroxy3-phenyl-isoxazole in 5 mL of isopropanol was slowly added dropwise to the reaction system, followed by the addition 0.101 g (1 mmol) of freshly distilled triethylamine. After the system was stirred at room temperature for 30 min, the reaction was hold at 60. After the completion of the reaction monitored by TLC, the reaction solution was concentrated under vacuum. The residue was directly separated by column chromatography (Vpetroleum ether:Vethyl acetate=5:1-2:1) to give the target compound of (6,7-bis(2-methoxyethoxy))-4-((3-(4-methylphenyl)-isoxazol-5-yl))-methoxy-)-quinazoline (i.e. Q-15 in the following Table). The other compounds were synthesized according to the synthetic process of (6,7-bis(2-methoxyethoxy))-4-((3-(4-methylphenyl)-isoxazol-5-yl))-methoxy-)-quinazoline. The structures were characterized by analytic methods such as IR, $^1$H NMR, ESI-MS, etc. The physical constants and spectral data of preferred compounds were indicated in the form of table.

The structures, numbers and designations of the preferred compounds are shown in the following table:

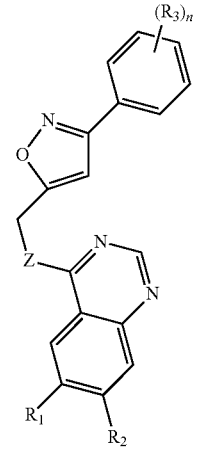

TABLE 1

Preferred compounds

| R$_1$, R$_2$ | Z | R$_3$ | No. | Designation |
|---|---|---|---|---|
| R$_1$ = R$_2$ = H | O | H | Q-1 | 4-((3-phenyl-isoxazol-5-yl)-methoxy-)-quinazoline |
| | | 4-CH$_3$ | Q-2 | 4-((3-(4-methylphenyl)-isoxazol-5-yl))-methoxy-)-quinazoline |
| | | 4-OCH$_3$ | Q-3 | 4-((3-(4-methoxyphenyl)-isoxazol-5-yl))-methoxy-)-quinazoline |
| | | 2-Cl | Q-4 | 4-((3-(2-chlorophenyl)-isoxazol-5-yl))-methoxy-)-quinazoline |
| | | 4-Cl | Q-5 | 4-((3-(4-chlorophenyl)-isoxazol-5-yl))-methoxy-)-quinazoline |
| | | 2,4-dichloro | Q-6 | 4-((3-(2,4-dichlorophenyl)-isoxazol-5-yl))-methoxy-)-quinazoline |
| | | 4-Br | Q-7 | 4-((3-(4-bromophenyl)-isoxazol-5-yl))-methoxy-)-quinazoline |

TABLE 1-continued

Preferred compounds

| $R_1, R_2$ | Z | $R_3$ | No. | Designation |
|---|---|---|---|---|
| | NH | H | Q-8 | 4-((3-phenyl-isoxazol-5-yl)-methylamino-)-quinazoline |
| | | 4-CH$_3$ | Q-9 | 4-((3-(4-methylphenyl)-isoxazol-5-yl))-methylamino-)-quinazoline |
| | | 4-OCH$_3$ | Q-10 | 4-((3-(4-methoxyphenyl)-isoxazol-5-yl))-methylamino-)-quinazoline |
| | | 2-Cl | Q-11 | 4-((3-(2-chlorophenyl)-isoxazol-5-yl))-methylamino-)-quinazoline |
| | | 4-Cl | Q-12 | 4-((3-(4-chlorophenyl)-isoxazol-5-yl))-methylamino-)-quinazoline |
| | | 2,4-dichloro | Q-13 | 4-((3-(2,4-dichlorophenyl)-isoxazol-5-yl))-methylamino-)-quinazoline |
| | | 4-Br | Q-14 | 4-((3-(4-bromophenyl)-isoxazol-5-yl))-methylamino-)-quinazoline |
| $R_1 = R_2 = -OCH_3$ | O | H | Q-15 | 6,7-dimethoxy-4-((3-phenyl-isoxazol-5-yl)-methoxy-)-quinazoline |
| | | 4-CH$_3$ | Q-16 | 6,7-dimethoxy-4-((3-(4-methylphenyl)-isoxazol-5-yl))-methoxy-)-quinazoline |
| | | 4-OCH$_3$ | Q-17 | 6,7-dimethoxy-4-((3-(4-methoxyphenyl)-isoxazol-5-yl))-methoxy-)-quinazoline |
| | | 2-Cl | Q-18 | 6,7-dimethoxy-4-((3-(2-chlorophenyl)-isoxazol-5-yl))-methoxy-)-quinazoline |
| | | 4-Cl | Q-19 | 6,7-dimethoxy-4-((3-(4-chlorophenyl)-isoxazol-5-yl))-methoxy-)-quinazoline |
| | | 2,4-dichloro | Q-20 | 6,7-dimethoxy-4-((3-(2,4-dichlorophenyl)-isoxazol-5-yl))-methoxy-)-quinazoline |
| | | 4-Br | Q-21 | 6,7-dimethoxy-4-((3-(4-bromophenyl)-isoxazol-5-yl))-methoxy-)-quinazoline |
| | NH | H | Q-22 | 6,7-dimethoxy-4-((3-phenyl-isoxazol-5-yl)-methylamino-)-quinazoline |
| | | 4-CH$_3$ | Q-23 | 6,7-dimethoxy-4-((3-(4-methylphenyl)-isoxazol-5-yl))-methylamino-)-quinazoline |
| | | 4-OCH$_3$ | Q-24 | 6,7-dimethoxy-4-((3-(4-methoxyphenyl)-isoxazol-5-yl))-methylamino-)-quinazoline |
| | | 2-Cl | Q-25 | 6,7-dimethoxy-4-((3-(2-chlorophenyl)-isoxazol-5-yl))-methylamino-)-quinazoline |
| | | 4-Cl | Q-26 | 6,7-dimethoxy-4-((3-(4-chlorophenyl)-isoxazol-5-yl))-methylamino-)-quinazoline |
| | | 2,4-dichloro | Q-27 | 6,7-dimethoxy-4-((3-(2,4-dichlorophenyl)-isoxazol-5-yl))-methylamino-)-quinazoline |
| | | 4-Br | Q-28 | 6,7-dimethoxy-4-((3-(4-bromophenyl)-isoxazol-5-yl))-methylamino-)-quinazoline |
| $R_1 = R_2 =$ CH$_3$OCH$_2$CH$_2$O— | O | H | Q-29 | (6,7-bis(2-methoxyethoxy))-4-((3-phenyl-isoxazol-5-yl)-methoxy-)-quinazoline |
| | | 4-CH$_3$ | Q-30 | (6,7-bis(2-methoxyethoxy))-4-((3-(4-methylphenyl)-isoxazol-5-yl)-methoxy-)-quinazoline |
| | | 4-OCH$_3$ | Q-31 | (6,7-bis(2-methoxyethoxy))-4-((3-(4-methoxyphenyl)-isoxazol-5-yl))-methoxy-)-quinazoline |
| | | 2-Cl | Q-32 | (6,7-bis(2-methoxyethoxy))-4-((3-(2-chlorophenyl)-isoxazol-5-yl))-methoxy-)-quinazoline |
| | | 4-Cl | Q-33 | (6,7-bis(2-methoxyethoxy))-4-((3-(4-chlorophenyl)-isoxazol-5-yl))-methoxy-)-quinazoline |
| | | 2,4-dichloro | Q-34 | (6,7-bis(2-methoxyethoxy))-4-((3-(2,4-dichlorophenyl)-isoxazol-5-yl)-methoxy-)-quinazoline |
| | | 4-Br | Q-35 | (6,7-bis(2-methoxyethoxy))-4-((3-(4-bromophenyl)-isoxazol-5-yl))-methoxy-)-quinazoline |
| | NH | H | Q-36 | (6,7-bis(2-methoxyethoxy))-4-((3-phenyl-isoxazol-5-yl)-methylamino-)-quinazoline |
| | | 4-CH$_3$ | Q-37 | (6,7-bis(2-methoxyethoxy))-4-((3-(4-methylphenyl)-isoxazol-5-yl))-methylamino-)-quinazoline |
| | | 4-OCH$_3$ | Q-38 | (6,7-bis(2-methoxyethoxy))-4-((3-(4-methoxyphenyl)-isoxazol-5-yl))-methylamino-)-quinazoline |
| | | 2-Cl | Q-39 | (6,7-bis(2-methoxyethoxy))-4-((3-(2-chlorophenyl)-isoxazol-5-yl))-methylamino-)-quinazoline |
| | | 4-Cl | Q-40 | (6,7-bis(2-methoxyethoxy))-4-((3-(4-chlorophenyl)-isoxazol-5-yl))-methylamino-)-quinazoline |
| | | 2,4-dichloro | Q-41 | (6,7-bis(2-methoxyethoxy))-4-((3-(2,4-dichlorophenyl)-isoxazol-5-yl))-methylamino-)-quinazolinr |
| | | 4-Br | Q-42 | (6,7-bis(2-methoxyethoxy))-4-((3-(4-bromophenyl)-isoxazol-5-yl))-methylamino-)-quinazoline |

TABLE 2

Physical constants, IR and MS data of the compounds in Table 1

| No. | Physical state | Melting point/ | IR/cm$^{-1}$ | MS (100%) |
|---|---|---|---|---|
| Q-1 | white solid | 115-117 | 3121, 2934, 1617, 1570, 1503, 1444, 1361, 1281, 1091, 958, 817 | 304 ((M + 1)$^+$, 100) |
| Q-2 | white solid | 143-144 | 3120, 2934, 1617, 1499, 1503, 1444, 1361, 1281, 1091, 958, 817 | 318 ((M + 1)$^+$, 100) |
| Q-3 | white solid | 172-173 | 3120, 2934, 1617, 1499, 1503, 1444, 1361, 1281, 1091, 958, 817 | 334 ((M + 1)$^+$, 100) |
| Q-4 | white solid | 104-105 | 3120, 2934, 1617, 1499, 1503, 1444, 1361, 1281, 1091, 958, 817 | 338 ((M + 1)$^+$, 100) |
| Q-5 | white solid | 145-148 | 3120, 2934, 1617, 1499, 1503, 1444, 1361, 1281, 1091, 958, 817 | 338 ((M + 1)$^+$, 100) |
| Q-6 | white solid | 146-147 | 3120, 2934, 1617, 1499, 1503, 1444, 1361, 1281, 1091, 958, 817 | 373 ((M + 2)$^+$, 20) |
| Q-7 | white solid | 158-160 | 3120, 2934, 1617, 1499, 1503, 1444, 1361, 1281, 1091, 958, 817 | |
| Q-8 | white solid | | 3237, 3079, 2927, 1590, 1544, 1433, 1232, 1106, 799 | 303 ((M + 1)$^+$, 100) |
| Q-9 | white solid | | 3237, 3079, 2927, 1590, 1544, 1433, 1232, 1106, 799 | 317 ((M + 1)$^+$, 100) |
| Q-10 | white solid | | 3237, 3079, 2927, 1590, 1544, 1433, 1232, 1106, 799 | 333 ((M + 1)$^+$, 100) |
| Q-11 | white solid | | 3237, 3079, 2927, 1590, 1544, 1433, 1232, 1106, 799 | 337 ((M + 1)$^+$, 100) |
| Q-12 | white solid | | 3237, 3079, 2927, 1590, 1544, 1433, 1232, 1106, 799 | 337 ((M + 1)$^+$, 100) |
| Q-13 | white solid | | 3237, 3079, 2927, 1590, 1544, 1433, 1232, 1106, 799 | 372 ((M + 2)$^+$, 20) |
| Q-14 | white solid | | 3237, 3079, 2927, 1590, 1544, 1433, 1232, 1106, 799 | |
| Q-15 | white solid | 163-164 | 3120, 2934, 1617, 1499, 1503, 1444, 1361, 1281, 1091, 958, 817 | 364 ((M + 1)$^+$, 100) |
| Q-16 | white solid | 169-171 | 3120, 2934, 1617, 1499, 1503, 1444, 1361, 1281, 1091, 958, 817 | 378 ((M + 1)$^+$, 100) |
| Q-17 | white solid | 158-161 | 3121, 2934, 1617, 1570, 1503, 1444, 1361, 1281, 1091, 958, 817 | 394 ((M + 1)$^+$, 100) |
| Q-18 | white solid | 163-165 | 3121, 2934, 1617, 1570, 1503, 1444, 1361, 1281, 1091, 958, 817 | 398 ((M + 1)$^+$, 100) |
| Q-19 | white solid | 176-178 | 3121, 2934, 1617, 1570, 1503, 1444, 1361, 1281, 1091, 958, 817 | 398 ((M + 1)$^+$, 100) |
| Q-20 | white solid | 185-187 | 3120, 2934, 1617, 1499, 1503, 1444, 1361, 1281, 1091, 958, 817 | 432 ((M + 1)$^+$, 100) |
| Q-21 | white solid | 178-179 | 3121, 2934, 1617, 1570, 1503, 1444, 1361, 1281, 1091, 958, 817 | 442 ((M + 1)$^+$, 100) |
| Q-22 | white solid | | 3237, 3079, 2927, 1590, 1544, 1433, 1232, 1106, 799 | 363 ((M + 1)$^+$, 100) |
| Q-23 | white solid | | 3237, 3079, 2927, 1590, 1544, 1433, 1232, 1106, 799 | 377 ((M + 1)$^+$, 100) |
| Q-24 | white solid | | 3237, 3079, 2927, 1590, 1544, 1433, 1232, 1106, 799 | 393 ((M + 1)$^+$, 100) |
| Q-25 | white solid | | 3237, 3079, 2927, 1590, 1544, 1433, 1232, 1106, 799 | 397 ((M + 1)$^+$, 100) |
| Q-26 | white solid | | 3237, 3079, 2927, 1590, 1544, 1433, 1232, 1106, 799 | 397 ((M + 1)$^+$, 100) |
| Q-27 | white solid | | 3237, 3079, 2927, 1590, 1544, 1433, 1232, 1106, 799 | 431 ((M + 1)$^+$, 100) |
| Q-28 | white solid | | 3237, 3079, 2927, 1590, 1544, 1433, 1232, 1106, 799 | 441 ((M + 1)$^+$, 100) |
| Q-29 | white solid | 112-113 | 3120, 2934, 1617, 1499, 1503, 1444, 1361, 1281, 1091, 958, 817 | 452 ((M + 1)$^+$, 100) |
| Q-30 | white solid | 115-117 | 3120, 2934, 1617, 1499, 1503, 1444, 1361, 1281, 1091, 958, 817 | 466 ((M + 1)$^+$, 100) |
| Q-31 | white solid | 136-137 | 3121, 2934, 1617, 1570, 1503, 1444, 1361, 1281, 1091, 958, 817 | 482 ((M + 1)$^+$, 100) |
| Q-32 | white solid | 133-134 | 3120, 2934, 1617, 1499, 1503, 1444, 1361, 1281, 1091, 958, 817 | 486 ((M + 1)$^+$, 100) |
| Q-33 | white solid | 117-118 | 3121, 2934, 1617, 1570, 1503, 1444, 1361, 1281, 1091, 958, 817 | 586 ((M + 1)$^+$, 100) |
| Q-34 | white solid | 121-122 | 3120, 2934, 1617, 1499, 1503, 1444, 1361, 1281, 1091, 958, 817 | 520 ((M + 1)$^+$, 100) |
| Q-35 | white solid | 119-120 | 3121, 2934, 1617, 1570, 1503, 1444, 1361, 1281, 1091, 958, 817 | 530 ((M + 1)$^+$, 100) |
| Q-36 | white solid | | 3237, 3079, 2927, 1590, 1544, 1433, 1232, 1106, 799 | 451 ((M + 1)$^+$, 100) |
| Q-37 | white solid | | 3237, 3079, 2927, 1590, 1544, 1433, 1232, 1106, 799 | 465 ((M + 1)$^+$, 100) |
| Q-38 | white solid | | 3237, 3079, 2927, 1590, 1544, 1433, 1232, 1106, 799 | 481 ((M + 1)$^+$, 100) |
| Q-39 | white solid | | 3237, 3079, 2927, 1590, 1544, 1433, 1232, 1106, 799 | 485 ((M + 1)$^+$, 100) |
| Q-40 | white solid | | 3237, 3079, 2927, 1590, 1544, 1433, 1232, 1106, 799 | 485 ((M + 1)$^+$, 100) |
| Q-41 | white solid | | 3237, 3079, 2927, 1590, 1544, 1433, 1232, 1106, 799 | 519 ((M + 1)$^+$, 100) |
| Q-42 | white solid | | 3237, 3079, 2927, 1590, 1544, 1433, 1232, 1106, 799 | 529 ((M + 1)$^+$, 100) |

TABLE 3

Physical constant of $^1$H NMR data of the compounds in Table 1

| No. | $^1$H NMR (DMSO-$d_6$) |
|---|---|
| Q-1 | 5.87 (s, 2H), 7.31(s, 1H, isoxazole-H), 7.51-7.54 (m, 3H), 7.71-7.76 (m, 1H), 7.89-7.92 (m, 2H), 7.98-8.0 1(m, 2H), 8.24-8.27 (m, 1H), 8.88(s, 1H). |
| Q-2 | 2.36 (s, 3H, CH$_3$), 5.86 (s, 2H, CH$_2$), 7.26(s, 1H, isoxazole-H), 7.33(d, 2H, J = 8.0 Hz), 7.71-7.74 (m, 1H), 7.80 (d, 2H, J = 8.0 Hz), 7.96-8.02 (m, 2H), 8.26 (d, 1H, J = 8.0 Hz), 8.88 (s, 1H). |
| Q-3 | 3.82(s, 3H, OCH$_3$), 5.85 (s, 2H, CH$_2$), 7.05-7.08(m, 2H), 7.24(s, 1H, isoxazole-H), 7.71-7.75 (m, 1H), 7.79-7.86(m, 2H), 7.96-8.03 (m, 2H), 8.26(d, 1H, J = 8.0 Hz), 8.87 (s, 1H). |
| Q-4 | 5.91 (s, 2H, CH$_2$), 7.19(s, 1H, isoxazole-H), 7.48-7.56 (m, 2H), 7.63-7.65 (m, 1H), 7 .67-7.75 (m, 2H), 7.97-8.02 (m, 2H), 8.24(d, 1H, J = 8.0 Hz), 8.87 (s, 1H). |
| Q-5 | 5.88 (s, 2H, CH$_2$), 7.34(s, 1H, isoxazole-H), 7.60(d, 2H, J = 8.4 Hz), 7.74-7.76(m, 1H), 7.93-7.95 (m, 2H), 7.98-8.01(m, 2H), 8.26(d, 1H, J = 7.6 Hz), 8.87 (s, 1H). |

TABLE 3-continued

Physical constant of $^1$H NMR data of the compounds in Table 1

| No. | $^1$H NMR (DMSO-$d_6$) |
|---|---|
| Q-6 | 5.90 (s, 2H, CH$_2$), 7.21 (s, 1H, isoxazole-H), 7.58-7.61 (m, 1H), 7.71-7.77 (m, 2H), 7.86(m, 1H), 7.96-8.03 (m, 2H), 8.24(d, 1H, J = 8.4 Hz), 8.88 (s, 1H). |
| Q-7 | 5.88 (s, 2H, CH$_2$), 7.34 (s, 1H, isoxazole-H), 7.60(d, 2H, J = 8.4 Hz), 7.74-7.76(m, 1H), 7.93-7.95 (m, 2H), 7.98-8.01(m, 2H), 8.26(d, 1H, J = 7.6 Hz), 8.88(s, 1H). |
| Q-8 | 4.29(t, J = 6.4 Hz, 1H, NH), 5.87-5.89 (m, 2H, CH$_2$), 7.32(s, 1H, isoxazole-H), 7.51-7.54 (m, 3H), 7.71-7.76 (m, 1H), 7.89-7.92 (m, 2H), 7.98-8.0 1(m, 2H), 8.24-8.27 (m, 1H), 8.88(s, 1H). |
| Q-9 | 2.36 (s, 3H, CH$_3$), 4.30(t, J = 6.6 Hz, 1H, NH), 5.86-5.85 (m, 2H, CH$_2$), 7.26(s, 1H, isoxazole-H), 7.33(d, 2H, J = 8.0 Hz), 7.71-7.74 (m, 1H), 7.80 (d, 2H, J = 8.0 Hz), 7.96-8.02 (m, 2H), 8.26 (d, 1H, J = 8.0 Hz), 8.88 (s, 1H). |
| Q-10 | 3.82(s, 3H, OCH$_3$), 4.31(t, J = 6.6 Hz, 1H, NH), 5.85-5.87 (m, 2H, CH$_2$), 7.05-7.08(m, 2H), 7.24(s, 1H, isoxazole-H), 7.71-7.75 (m, 1H), 7.79-7.86(m, 2H), 7.96-8.03 (m, 2H), 8.26(d, 1H, J = 8.0 Hz), 8.87 (s, 1H). |
| Q-11 | 4.31(t, J = 6.6 Hz, 1H, NH), 5.91-5.92 (m, 2H, CH$_2$), 7.19(s, 1H, isoxazole-H), 7.48-7.56 (m, 2H), 7.63-7.65 (m, 1H), 7 .67-7.75 (m, 2H), 7.97-8.02 (m, 2H), 8.24(d, 1H, J = 8.0 Hz), 8.87 (s, 1H). |
| Q-12 | 4.30(t, J = 6.6 Hz, 1H, NH), 5.88-5.89 (m, 2H, CH$_2$), 7.34(s, 1H, isoxazole-H), 7.60(d, 2H, J = 8.4 Hz), 7.74-7.76(m, 1H), 7.93-7.95 (m, 2H), 7.98-8.01(m, 2H), 8.26(d, 1H, J = 7.6 Hz), 8.87 (s, 1H). |
| Q-13 | 4.29(t, J = 6.6 Hz, 1H, NH), 5.90-5.91 (m, 2H, CH$_2$), 7.21 (s, 1H, isoxazole-H), 7.58-7.61 (m, 1H), 7.71-7.77 (m, 2H), 7.86(m, 1H), 7.96-8.03 (m, 2H), 8.24(d, 1H, J = 8.4 Hz), 8.88 (s, 1H). |
| Q-14 | 4.29(t, J = 6.6 Hz, 1H, NH), 5.88-5.90 (m, 2H, CH$_2$), 7.34 (s, 1H, isoxazole-H), 7.60(d, 2H, J = 8.4 Hz), 7.74-7.76(m, 1H), 7.93-7.95 (m, 2H), 7.98-8.01(m, 2H), 8.26(d, 1H, J = 7.6 Hz), 8.88(s, 1H). |
| Q-15 | 3.95(s, 6H, 3CH$_3$), 5.84(s, 2H, CH$_2$), 7.24 (s, 1H, isoxazole-H), 7.38(d, 2H, J = 6.8 Hz), 7.51-7.53 (m, 2H), 7.65-7.72(m, 1H), 7.89-7.91(m, 2H), 8.70(s, 1H). |
| Q-16 | 2.36(s, 3H, CH$_3$), 3.97(s, 6H, 2CH$_3$), 5.83(s, 2H, CH$_2$), 7.23(s, 1H, isoxazole-H), 7.33(d, 2H, J = 8.0 Hz), 7.37(d, 2H, J = 6.0 Hz), 7.79(d, 2H, J = 8.0 Hz), 8.70(s, 1H). |
| Q-17 | 3.82(s, 3H, OCH$_3$), 3.97(s, 6H, 2CH$_3$), 5.82(s, 2H, CH$_2$), 7.07(d, 2H, J = 7.6 Hz), 7.20(s, 1H, isoxazole-H), 7.37(d, 2H, J = 4.8 Hz), 7.84(d, 2H, J = 7.6 Hz), 8.69(s, 1H). |
| Q-18 | 3.97(s, 6H, 2CH$_3$), 5.87(s, 2H, CH$_2$), 7.16(s, 1H, isoxazole-H), 7.37(m, 2H), 7.48-7.56(m, 2H), 7.64-7.73(m, 2H), 8.70(s, 1H). |
| Q-19 | 3.97(s, 6H, 2CH$_3$), 5.85(s, 2H, CH$_2$), 7.30(s, 1H, isoxazole-H), 7.37(d, 2H, J = 6.4 Hz), 7.60(d, 2H, J = 8.4 Hz), 7.94(d, 2H, J = 8.8 Hz), 8.69(s, 1H). |
| Q-20 | 3.91(s, 6H, 2CH$_3$), 5.87(s, 2H, CH$_2$), 7.17(s, 1H, isoxazole-H), 7.37(m, 2H), 7.58-7.60(m, 1H), 7.76(d, 1H, J = 8.4 Hz), 7.84-7.85(m, 1H), 8.70(s, 1H). |
| Q-21 | 3.97 (s, 6H, 2CH$_3$), 5.84 (s, 2H, CH$_2$), 7.29 (s, 1H, isoxazole-H), 7.37(d, 2H, J = 8.0 Hz), 7.73 (d, 1H, J = 8.4 Hz), 7.86 (d, 1H, J = 8.4 Hz), 8.69 (s, 1H). |
| Q-22 | 3.95(s, 6H, 3CH$_3$), 4.29(t, J = 6.6 Hz, 1H, NH), 5.84-5.85(m, 2H, CH$_2$), 7.24 (s, 1H, isoxazole-H), 7.38(d, 2H, J = 6.8 Hz), 7.51-7.53 (m, 2H), 7.65-7.72(m, 1H), 7.89-7.91(m, 2H), 8.70(s, 1H). |
| Q-23 | 2.36(s, 3H, CH$_3$), 3.97(s, 6H, 2CH$_3$), 4.29(t, J = 6.6 Hz, 1H, NH), 5.83-5.85(m, 2H, CH$_2$), 7.23(s, 1H, isoxazole-H), 7.33(d, 2H, J = 8.0 Hz), 7.37(d, 2H, J = 6.0 Hz), 7.79(d, 2H, J = 8.0 Hz), 8.70(s, 1H). |
| Q-24 | 3.82(s, 3H, OCH$_3$), 3.97(s, 6H, 2CH$_3$), 4.29(t, J = 6.6 Hz, 1H, NH), 5.82-5.83(m, 2H, CH$_2$), 7.07(d, 2H, J = 7.6 Hz), 7.20(s, 1H, isoxazole-H), 7.37(d, 2H, J = 4.8 Hz), 7.84(d, 2H, J = 7.6 Hz), 8.69(s, 1H). |
| Q-25 | 3.97(s, 6H, 2CH$_3$), 4.31(t, J = 6.6 Hz, 1H, NH), 5.87-5.89(m, 2H, CH$_2$), 7.16(s, 1H, isoxazole-H), 7.37(m, 2H), 7.48-7.56(m, 2H), 7.64-7.73(m, 2H), 8.70(s, 1H). |
| Q-26 | 3.97(s, 6H, 2CH$_3$), 4.31(t, J = 6.6 Hz, 1H, NH), 5.85-5.86(m, 2H, CH$_2$), 7.30(s, 1H, isoxazole-H), 7.37(d, 2H, J = 6.4 Hz), 7.60(d, 2H, J = 8.4 Hz), 7.94(d, 2H, J = 8.8 Hz), 8.69(s, 1H). |
| Q-27 | 3.91(s, 6H, 2CH$_3$), 4.31(t, J = 6.6 Hz, 1H, NH), 5.87-5.88(m, 2H, CH$_2$), 7.17(s, 1H, isoxazole-H), 7.37(m, 2H), 7.58-7.60(m, 1H), 7.76(d, 1H, J = 8.4 Hz), 7.84-7.85(m, 1H), 8.70(s, 1H). |
| Q-28 | 3.97 (s, 6H, 2CH$_3$), 4.31(t, J = 6.6 Hz, 1H, NH), 5.84-5.85 (m, 2H, CH$_2$), 7.29 (s, 1H, isoxazole-H), 7.37(d, 2H, J = 8.0 Hz), 7.73 (d, 1H, J = 8.4 Hz), 7.86 (d, 1H, J = 8.4 Hz), 8.69 (s, 1H). |
| Q-29 | 3.35(s, 6H, 2CH$_3$), 3.72-3.76(m, 4H, 2CH$_2$), 4.26-4.33(m, 4H, 2CH$_2$), 5.83(s, 2H, CH$_2$), 7.23 (s, 1H, isoxazole-H), 7.42(d, 2H, J = 12.0 Hz), 7.50-7.54(m, 3H), 7.89-7.91(m, 2H), 8.69(s, 1H). |
| Q-30 | 2.36(s, 3H, Ph-CH$_3$), 3.36(s, 6H, 2CH$_3$), 3.72-3.76(m, 4H, 2CH$_2$), 4.25-4.33(m, 4H, 2CH$_2$), 5.81 (s, 2H, CH$_2$), 7.23 (s, 1H, isoxazole-H), 7.31-7.35(m, 2H), 7.38-7.41(m, 2H), 7.77-7.79(m, 2H), 8.68(s, 1H). |
| Q-31 | 3.34 (s, 6H, 2CH$_3$), 3.72-3.76 (m, 4H, 2CH$_2$), 3.81 (s, 3H, Ph-OCH$_3$), 4.25-4.33 (m, 4H, 2CH$_2$), 5.80 (s, 2H, CH$_2$), 7.07(d, 2H, J = 8.8 Hz), 7.20 (s, 1H, isoxazole-H), 7.41 (d, 2H, J = 12.0 Hz), 8.69 (s, 1H). |
| Q-32 | 3.35(s, 6H, 2CH$_3$), 3.72-3.76(m, 4H, 2CH$_2$), 4.26-4.33(m, 4H, 2CH$_2$), 5.86(s, 2H, CH$_2$), 7.16(s, 1H, isoxazole-H), 7.40(d, 2H, J = 12.8 Hz), 7.49-7.65(m, 2H), 7.71-7.72(m, 2H), 8.69(s, 1H). |

TABLE 3-continued

Physical constant of $^1$H NMR data of the compounds in Table 1

| No. | $^1$H NMR (DMSO-d$_6$) |
|---|---|
| Q-33 | 3.35(s, 6H, 2CH$_3$), 3.72-3.76(m, 4H, 2CH$_2$), 4.25-4.33(m, 4H, 2CH$_2$), 5.83(s, 2H, CH$_2$), 7.30(s, 1H, isoxazole-H), 7.42(d, 2H, J = 13.2 Hz), 7.58-7.60(m, 2H), 7.92-7.94(m, 2H), 8.68(s, 1H). |
| Q-34 | 3.35(s, 6H, 2CH$_3$), 3.72-3.76(m, 4H, 2CH$_2$), 4.25-4.33(m, 4H, 2CH$_2$), 5.86(s, 2H, CH$_2$), 7.18(s, 1H, isoxazole-H), 7.40(d, 2H, J = 11.2 Hz), 7.58-7.61(m, 1H), 7.74-7.76(m, 1H), 7.85-7.86(m, 1H), 8.69(s, 1H). |
| Q-35 | 3.36(s, 6H, 2CH$_3$), 3.72-3.76(m, 4H, 2CH$_2$), 4.25-4.33(m, 4H, 2CH$_2$), 5.83(s, 2H, CH$_2$), 7.30(s, 1H, isoxazole-H), 7.40(d, 2H, J = 12.8 Hz), 7.72-7.74(m, 2H), 7.85-7.87(m, 2H), 8.68(s, 1H). |
| Q-36 | 3.35(s, 6H, 2CH$_3$), 3.72-3.76(m, 4H, 2CH$_2$), 4.26-4.30(m, 4H, 2CH$_2$), 4.31(t, J = 6.6 Hz, 1H, NH), 5.83-5.85(m, 2H, CH$_2$), 7.23 (s, 1H, isoxazole-H), 7.42(d, 2H, J = 12.0 Hz), 7.50-7.54(m, 3H), 7.89-7.91(m, 2H), 8.69(s, 1H). |
| Q-37 | 2.36(s, 3H, Ph-CH$_3$), 3.36(s, 6H, 2CH3), 3.72-3.76(m, 4H, 2CH$_2$), 4.25-4.33(m, 4H, 2CH$_2$), 4.34(t, J = 6.6 Hz, 1H, NH), 5.81-5.83 (m, 2H, CH$_2$), 7.23 (s, 1H, isoxazole-H), 7.31-7.35(m, 2H), 7.38-7.41(m, 2H), 7.77-7.79(m, 2H), 8.68(s, 1H). |
| Q-38 | 3.34 (s, 6H, 2CH$_3$), 3.72-3.76 (m, 4H, 2CH$_2$), 3.81 (s, 3H, Ph-OCH$_3$), 4.25-4.33 (m, 4H, 2CH$_2$), 4.34(t, J = 6.6 Hz, 1H, NH), 5.80-5.82 (m, 2H, CH$_2$), 7.07(d, 2H, J = 8.8 Hz), 7.20 (s, 1H, isoxazole-H), 7.41 (d, 2H, J = 12.0 Hz), 8.69 (s, 1H). |
| Q-39 | 3.35(s, 6H, 2CH$_3$), 3.72-3.76(m, 4H, 2CH$_2$), 4.26-4.33(m, 4H, 2CH$_2$), 4.35(t, J = 6.6 Hz, 1H, NH), 5.86-5.88(m, 2H, CH$_2$), 7.16(s, 1H, isoxazole-H), 7.40(d, 2H, J = 12.8 Hz), 7.49-7.65(m, 2H), 7.71-7.72(m, 2H), 8.69(s, 1H). |
| Q-40 | 3.35(s, 6H, 2CH$_3$), 3.72-3.76(m, 4H, 2CH$_2$), 4.25-4.33(m, 4H, 2CH$_2$), 4.35(t, J = 6.6 Hz, 1H, NH), 5.83-5.85(m, 2H, CH$_2$), 7.30(s, 1H, isoxazole-H), 7.42(d, 2H, J = 13.2 Hz), 7.58-7.60(m, 2H), 7.92-7.94(m, 2H), 8.68(s, 1H). |
| Q-41 | 3.35(s, 6H, 2CH$_3$), 3.72-3.76(m, 4H, 2CH$_2$), 4.25-4.33(m, 4H, 2CH$_2$), 4.34(t, J = 6.6 Hz, 1H, NH), 5.86-5.87(m, 2H, CH$_2$), 7.18(s, 1H, isoxazole-H), 7.40(d, 2H, J = 11.2 Hz), 7.58-7.61(m, 1H), 7.74-7.76(m, 1H), 7.85-7.86(m, 1H), 8.69(s, 1H). |
| Q-42 | 3.36(s, 6H, 2CH$_3$), 3.72-3.76(m, 4H, 2CH$_2$), 4.25-4.33(m, 4H, 2CH$_2$), 4.34(t, J = 6.6 Hz, 1H, NH), 5.83-5.85(m, 2H, CH$_2$), 7.30(s, 1H, isoxazole-H), 7.40(d, 2H, J = 12.8 Hz), 7.72-7.74(m, 2H), 7.85-7.87(m, 2H), 8.68(s, 1H). |

Example 4

Preparation of 4-((3-phenyl-isoxazol-5-yl)-methoxy-)-quinazoline hydrochloride and acetate (1) 4-((3-phenyl-isoxazol-5-yl)-methoxy-)-quinazoline hydrochloride 0.5 mmol of 4-((3-phenyl-isoxazol-5-yl)-methoxy-)-quinazoline was added in 20 mL mixing solution of 5% hydrochloric acid solution and methanol (V:V=1:1), and dissolved by stirring under slightly heating. The mixture was slowly evaporated and crystallized at room temperature to afford 4-((3-phenyl-isoxazol-5-yl)-methoxy-)-quinazoline hydrochloride as a white solid in 68% yield.

(2) preparation of 4-((3-phenyl-isoxazol-5-yl)-methoxy-)-quinazoline acetate 0.5 mmol of 4-((3-phenyl-isoxazol-5-yl)-methoxy-)-quinazoline was added to a 50 mL single-necked round-bottom flask containing 10 mL of dry dichloromethane. 2 mL of glacial acetic acid was added under stirring. The mixture was stirred for 1-2 hours at 30-40, cooled down, and then crystallized under refrigeration, filtered and dried under vacuum to afford 4-((3-phenyl-isoxazol-5-yl)-methoxy-)-quinazoline acetate as a colorless solid in 58% yield.

TABLE 4

Salts formed from the compounds represented by formula (I) respectively with organic acid or inorganic acid
Salts formed from the compounds represented by formula (I) respectively with organic acids or inorganic acids

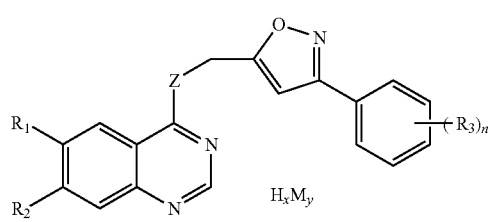

| | $H_xM_y$ | Salts formed from the compounds represented by formula (I) with inorganic acids |
|---|---|---|
| | Hydrochloride | Hydrochloride |
| | Nitric acid | Nitrate |
| | Sulfuric acid | Sulfate |
| | Phosphoric acid | Phosphate |

TABLE 4-continued

Salts formed from the compounds represented by formula (I) respectively with organic acid or inorganic acid
Salts formed from the compounds represented by formula (I) respectively with organic acids or inorganic acids

| $R_xCOOH$ | Salts formed from the compounds represented by formula (I) with organic acids |
|---|---|
| Formic acid | Formate |
| Acetic acid | Actate |
| Oxalic acid | oxalate |
| Citric acid | Citrate |
| Fumaric acid | Fumarate |
| Maleic acid | Maleate |
| Malic acid | Malate |
| Lactic acid | Lactate |
| Tartaric acid | Tartrate |
| P-toluenesulfonic acid | P-toluenesulfonate |
| Trifluoroacetic acid | Trifluoroacetate |
| Amino acid | Amino acid salt |

Example 5

Biological Activity Test

Quinazoline compounds represented by formula (I) and their pharmaceutically acceptable salts according to the present invention are used as EGFR inhibitors. The activity of the particularized compounds for inhibiting EGFR was determined by Enzyme-Linked Immunosorbent assay.

Detailed experimental procedure is as follows:

(1) Kinase reaction substrate poly(Glu,Tyr)$_{4:1}$ was diluted to 20 μg/mL with potassium-free PBS, and the microplates were coated. After the reaction was for 12-16 h at 37° C., the liquid in the wells was removed.

(2) The plates were washed with T-PBS for three times, 10 min each time.

(3) The microplates were dried in an oven at 37.

(4) The samples to be tested were added into the wells of the coated microplates (wherein the samples to be tested were formulated to a $1 \times 10^{-2}$M stock solution with DMSO, and diluted to the desired concentration with reaction buffer before use. The resulted solution was added into the wells and then allowed to achieve the corresponding final concentration in 100 μL reaction system.

(5) the addition of ATP and tested tyrosine kinases

ATP solution diluted with reaction buffer (the final concentration of ATP is 5 μM) and the tested tyrosine kinases solution diluted with reaction buffer were added. The total volume of the reaction is 100 μL. Meanwhile the negative control wells and the control wells without enzyme were set up.

(6) The reaction system was placed in a wet box, and shaked for 1 hour at 37° C. shielding from light. After the reaction was complete, the plates were washed with T-PBS for three times.

(7) Antibody PY99 was added into each well (100 μL/well); and the plates were shaked for 30 min at 37° C. After the reaction was complete, the plates were washed with T-PBS for three times.

(8) 100 μL horseradish peroxidase-labeled goat anti-mouse IgG was added into each well, and the plates were shaked for 30 min at 37° C. The plates were washed with T-PBS for three times.

(9) 100 μL OPD developing liquid was added in each well, and was reacted for 1-10 min at room temperature shielding from light.

(10) 2M $H_2SO_4$ was added into each well to terminate the reaction. $A_{490}$ value was determined using wavelength-tunable microplate reader. The inhibition ratio can be calculated by the following formula:

$$\text{inhibition rate (\%)} = \frac{OD \text{ value of control well without enzyme} - OD \text{ value of compound}}{OD \text{ value of control well without enzyme} - OD \text{ value of negative control}} \times 100$$

According to the above-described activity test method, the activity of inhibiting EGFR enzyme of the compounds represented by formula (I) or salts thereof were calculated.

TABLE 5

Activity test results of the activity of inhibiting EGFR of some compounds at a concentration of 100 μM

| Compound No. | EGFR inhibition rate (%) | Compound No. | EGFR inhibition rate (%) |
|---|---|---|---|
| Q-1 | 18.0 | Q-3 | 7.3 |
| Q-4 | 25.8 | Q-5 | 16.7 |
| Q-6 | 22.7 | Q-7 | 15.7 |
| Q-15 | 30.7 | Q-17 | 47.0 |
| Q-18 | 1.2 | Q-19 | 14.5 |
| Q-20 | 29.8 | Q-21 | 30.9 |
| Q-29 | 27.7 | Q-30 | 20.4 |
| Q-31 | 38.2 | Q-32 | 11.8 |
| Q-33 | 14.1 | Q-34 | 7.8 |
| Q-35 | 6.4 | | |

The invention claimed is:

1. A quinazoline compound of formula (I) or a pharmaceutically acceptable salt thereof,

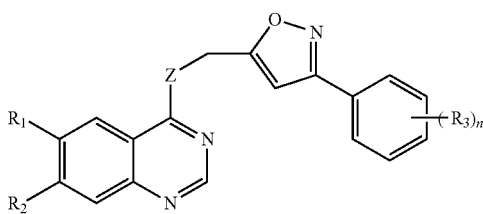

(I)

wherein $R_1$ and $R_2$ are independently selected from H, $C_1$-$C_6$ alkoxy, halo-$C_1$-$C_6$ alkoxy, $C_1$-$C_6$ alkoxy-$C_1$-$C_6$ alkoxy, $C_3$-$C_8$ cycloalkoxy, or $C_3$-$C_8$ heterocycloalkoxy containing at least one of heteroatoms selected from N, O, or S, Z is —$NR_4$—, $C(R_5)_2$, S, or —O—, wherein $R_4$ is H or $C_1$-$C_3$ alkyl, $R_5$ is the same or different, selected from H or $C_1$-$C_3$ alkyl, $R_3$ is selected from H, halogen, $C_1$-$C_6$ alkyl, $C_1$-$C_6$ alkoxy, or halo-$C_1$-$C_6$ alkyl, and n is an integer from 0 to 5, wherein the following compound is disclaimed

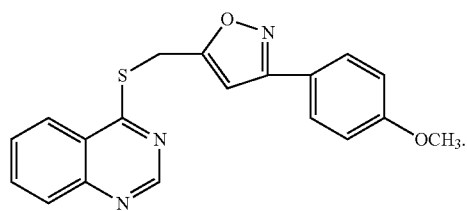 [SMILES: COc1ccc(-c2cc(CSc3ncnc4ccccc34)on2)cc1]

2. The quinazoline compound or the pharmaceutically acceptable salt thereof according to claim 1,
wherein $R_1$ and $R_2$ are independently selected from H, $C_1$-$C_3$ alkoxy, $C_1$-$C_6$ alkoxy-$C_1$-$C_6$ alkoxy, or $C_3$-$C_8$ heterocycloalkoxy containing at least one of heteroatoms selected from N, O, or S,
Z is —NH—, $CH_2$, or —O—, and
$R_3$ is selected from H, fluoro, chloro, bromo, methyl, methoxy, or trifluoromethyl; and n is 1, 2, 3, or 4.

3. The quinazoline compound or the pharmaceutically acceptable salt thereof according to claim 2, wherein n is 2 or 3.

4. The quinazoline compound or the pharmaceutically acceptable salt thereof according to claim 1,
wherein Z is —NH— or —O—,
$R_1$ and $R_2$ are independently selected from H, $C_1$-$C_3$ alkoxy, or $C_1$-$C_3$ alkoxy-$C_1$-$C_3$ alkoxy, and
$R_3$ is at the ortho- or para-position in an isoxazole ring, and is selected from 4-fluoro, 4-chloro, 2-chloro, 4-bromo, 2,4-dichloro, 4-methyl, 4-methoxy, H, 4-trifluoromethyl, or 2,4-dimethoxy.

5. A quinazoline compound or a pharmaceutically acceptable salt thereof, wherein said quinazoline compound is selected from:
4-((3-phenyl-isoxazol-5-yl)methoxy-)-quinazoline;
4-((3-(4-fluorophenyl)isoxazol-5-yl))-methoxy-)-quinazoline;
4-((3-(4-chlorophenyl)-isoxazol-5-yl))-methoxy-)-quinazoline;
4-((3-(2-chlorophenyl)-isoxazol-5-yl))-methoxy-)-quinazoline;
4-((3-(4-bromophenyl)-isoxazol-5-yl))-methoxy-)-quinazoline;
4-((3-(2,4-dichlorophenyl)-isoxazol-5-yl))-methoxy-)-quinazoline;
4-((3-(4-methylphenyl)-isoxazol-5-yl))-methoxy-)-quinazoline;
4-((3-(4-methoxyphenyl)-isoxazol-5-yl))-methoxy-)-quinazoline;
4-((3-(4-trifluoromethylphenyl)-isoxazol-5-yl))-methoxy-)-quinazoline;
4-((3-(2,4-dimethoxyphenyl)-isoxazol-5-yl))-methoxy-)-quinazoline;
6,7-dimethoxy-4-((3-phenyl-isoxazol-5-yl)-methoxy-)-quinazoline;
6,7-dimethoxy-4-((3-(4-fluorophenyl)-isoxazol-5-yl))-methoxy-)-quinazoline;
6,7-dimethoxy-4-((3-(4-chlorophenyl)-isoxazol-5-yl))-methoxy-)-quinazoline;
6,7-dimethoxy-4-((3-(2-chlorophenyl)-isoxazol-5-yl))-methoxy-)-quinazoline;
6,7-dimethoxy-4-((3-(4-bromophenyl)-isoxazol-5-yl))-methoxy-)-quinazoline;
6,7-dimethoxy-4-((3-(2,4-dichlorophenyl)-isoxazol-5-yl))-methoxy-)-quinazoline;
6,7-dimethoxy-4-((3-(4-methylphenyl)-isoxazol-5-yl))-methoxy-)-quinazoline;
6,7-dimethoxy-4-((3-(4-methoxyphenyl)-isoxazol-5-yl))-methoxy-)-quinazoline;
6,7-dimethoxy-4-((3-(4-trifluoromethylphenyl)-isoxazol-5-yl))-methoxy-)-quinazoline;
6,7-dimethoxy-4-((3-(2,4-dimethoxyphenyl)-isoxazol-5-yl))-methoxy-)-quinazoline;
(6,7-bis(2-methoxyethoxy))-4-((3-phenyl-isoxazol-5-yl)-methoxy-)-quinazoline;
(6,7-bis(2-methoxyethoxy))-4-((3-(4-fluorophenyl)-isoxazol-5-yl))-methoxy-)-quinazoline;
(6,7-bis(2-methoxyethoxy))-4-((3-(4-chlorophenyl)-isoxazol-5-yl))-methoxy-)-quinazoline;
(6,7-bis(2-methoxyethoxy))-4-((3-(2-chlorophenyl)-isoxazol-5-yl))-methoxy-)-quinazoline;
(6,7-bis(2-methoxyethoxy))-4-((3-(4-bromophenyl)-isoxazol-5-yl))-methoxy-)-quinazoline;
(6,7-bis(2-methoxyethoxy))-4-((3-(2,4-dichlorophenyl)-isoxazol-5-yl))-methoxy-)-quinazolin;
(6,7-bis(2-methoxyethoxy))-4-((3-(4-methylphenyl)-isoxazol-5-yl))-methoxy-)-quinazoline;
(6,7-bis(2-methoxyethoxy))-4-((3-(4-methoxyphenyl)-isoxazol-5-yl))-methoxy-)-quinazoline;
(6,7-bis(2-methoxyethoxy))-4-((3-(4-trifluoromethylphenyl)-isoxazol-5-yl))-methoxy-)-quinazoline;
(6,7-bis(2-methoxyethoxy))-4-((3-(2,4-dimethoxyphenyl)-isoxazol-5-yl))-methoxy-)-quinazoline;
4-((3-phenyl-isoxazol-5-yl)methylamino-)-quinazoline;
4-((3-(4-fluorophenyl)-isoxazol-5-yl))-methylamino-)-quinazoline;
4-((3-(4-chlorophenyl)-isoxazol-5-yl))-methylamino-)-quinazoline;
4-((3-(2-chlorophenyl)-isoxazol-5-yl))-methylamino-)-quinazoline;
4-((3-(4-bromophenyl)-isoxazol-5-yl))-methylamino-)-quinazoline;
4-((3-(2,4-dichlorophenyl)-isoxazol-5-yl))-methylamino-)-quinazoline;
4-((3-(4-methylphenyl)-isoxazol-5-yl))-methylamino-)-quinazoline;
4-((3-(4-methoxyphenyl)-isoxazol-5-yl))-methylamino-)-quinazoline;

4-((3-(4-trifluoromethylphenyl)-isoxazol-5-yl))-methylamino-)-quinazoline;
4-((3-(2,4-dimethoxyphenyl)-isoxazol-5-yl))-methylamino-)-quinazoline;
6,7-dimethoxy-4-((3-phenyl-isoxazol-5-yl)-methylamino-)-quinazoline;
6,7-dimethoxy-4-((3-(4-fluorophenyl)-isoxazol-5-yl))-methylamino-)-quinazoline;
6,7-dimethoxy-4-((3-(4-chlorophenyl)-isoxazol-5-yl))-methylamino-)-quinazoline;
6,7-dimethoxy-4-((3-(2-chlorophenyl)-isoxazol-5-yl))-methylamino-)-quinazoline;
6,7-dimethoxy-4-((3-(4-bromophenyl)-isoxazol-5-yl))-methylamino-)-quinazoline;
6,7-dimethoxy-4-((3-(2,4-dichlorophenyl)-isoxazol-5-yl))-methylamino-)-quinazoline;
6,7-dimethoxy-4-((3-(4-methylphenyl)-isoxazol-5-yl))-methylamino-)-quinazoline;
6,7-dimethoxy-4-((3-(4-methoxyphenyl)-isoxazol-5-yl))-methylamino-)-quinazoline;
6,7-dimethoxy-4-((3-(4-trifluoromethylphenyl)-isoxazol-5-yl))-methylamino-)-quinazoline;
6,7-dimethoxy-4-((3-(2,4-dimethoxyphenyl)-isoxazol-5-yl))-methylamino-)-quinazoline;
(6,7-bis(2-methoxyethoxy))-4-((3-phenyl-isoxazol-5-yl)-methylamino-)-quinazoline;
(6,7-bis(2-methoxyethoxy))-4-((3-(4-fluorophenyl)-isoxazol-5-yl))-methylamino-)-quinazoline;
(6,7-bis(2-methoxyethoxy))-4-((3-(4-chlorophenyl)-isoxazol-5-yl))-methylamino-)-quinazoline;
(6,7-bis(2-methoxyethoxy))-4-((3-(2-chlorophenyl)-isoxazol-5-yl))-methylamino-)-quinazoline;
(6,7-bis(2-methoxyethoxy))-4-((3-(4-bromophenyl)-isoxazol-5-yl))-methylamino-)-quinazoline;
(6,7-bis(2-methoxyethoxy))-4-((3-(2,4-dichlorophenyl)-isoxazol-5-yl))-methylamino-)-quinazoline;
(6,7-bis(2-methoxyethoxy))-4-((3-(4-methylphenyl)-isoxazol-5-yl))-methylamino-)-quinazoline;
(6,7-bis(2-methoxyethoxy))-4-((3-(4-methoxyphenyl)-isoxazol-5-yl))-methylamino-)-quinazoline;
(6,7-bis(2-methoxyethoxy))-4-((3-(4-trifluoromethylphenyl)-isoxazol-5-yl))-methylamino-)-quinazoline; or
(6,7-bis(2-methoxyethoxy))-4-((3-(2,4-dimethoxyphenyl)-isoxazol-5-yl))-methylamino-)-quinazoline.

6. A pharmaceutical composition, comprising a quinazoline compound represented by formula (I) according to claim 1, or a pharmaceutically acceptable salt thereof, and at least one pharmaceutically acceptable excipient or carrier.

7. A method for preparing a drug composition, comprising:
obtaining a pharmaceutically effective amount of a quinazoline compound of formula (I) according to claim 1 or one or more of its pharmaceutically acceptable salts;
mixing the quinazoline compound or its pharmaceutically acceptable salts with a pharmaceutically acceptable excipient or a carrier,
wherein the drug composition is for treating tumour or cancer.

8. A method of preparing a quinazoline compound represented by formula (I) according to claim 1 or a pharmaceutically acceptable salt thereof, comprising:

reacting 6,7-Disubstituted-4-chloro-quinazoline (formula II) and 3-substituted phenyl-5-hydroxymethyl-isoxazole (formula III) or 3-substituted phenyl-5-aminomethyl-isoxazole (formula IV) in a system of a dry organic solvent and an alkaline deacid reagent; and
obtaining a compound of formula I-1 or a compound of formula I-2, respectively

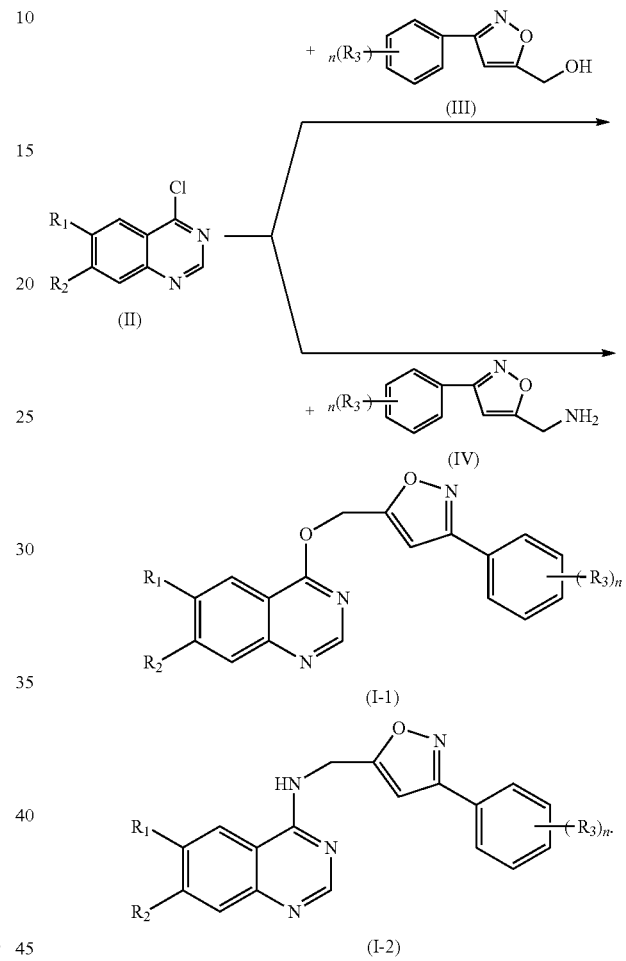

9. The method of claim 8, further comprising:
protecting a functional group in 6,7-disubstituted-4-chloro-quinazoline (formula II); and
deprotecting the functional group after reacting 6,7-disubstituted-4-chloro-quinazoline (formula II) with 3-substituted phenyl-5-hydroxymethyl-isoxazole (formula III) or 3-substituted phenyl-5-aminomethyl-isoxazole (formula IV).

10. The method of claim 8, further comprising: forming a pharmaceutically acceptable salt of the compound of formula I-1 or formula I-2.

* * * * *